(12) United States Patent
Subagyo et al.

(10) Patent No.: US 8,487,297 B2
(45) Date of Patent: Jul. 16, 2013

(54) FIELD EFFECT TRANSISTOR, METHOD FOR MANUFACTURING THE SAME, AND BIOSENSOR

(75) Inventors: Agus Subagyo, Hokkaido (JP);
Motonori Nakamura, Hokkaido (JP);
Tomoaki Yamabayashi, Hokkaido (JP);
Osamu Takahashi, Hokkaido (JP);
Hiroaki Kikuchi, Hokkaido (JP);
Katsunori Kondo, Hokkaido (JP)

(73) Assignees: Mitsumi Electric Co., Ltd., Tokyo (JP);
Arkray, inc., Kyoto (JP)

( * ) Notice: Subject to any disclaimer, the term of this patent is extended or adjusted under 35 U.S.C. 154(b) by 27 days.

(21) Appl. No.: 13/143,256

(22) PCT Filed: Dec. 25, 2009

(86) PCT No.: PCT/JP2009/007253
§ 371 (c)(1),
(2), (4) Date: Aug. 19, 2011

(87) PCT Pub. No.: WO2010/079573
PCT Pub. Date: Jul. 15, 2010

(65) Prior Publication Data
US 2011/0291075 A1    Dec. 1, 2011

(30) Foreign Application Priority Data

Jan. 9, 2009 (JP) .................. 2009-003628

(51) Int. Cl.
*H01L 29/06* (2006.01)
(52) U.S. Cl.
USPC ............... 257/29; 438/49; 977/746; 977/938
(58) Field of Classification Search
USPC ............. 257/29, 253, 414, E51.049; 438/49; 977/746, 847, 938, 957
See application file for complete search history.

(56) References Cited

U.S. PATENT DOCUMENTS

| 7,439,562 B2 * | 10/2008 | Auvray et al. ............ 257/253 |
| 2007/0278388 A1 | 12/2007 | Hirose et al. |
| 2009/0008629 A1 | 1/2009 | Matsumoto et al. |
| 2009/0224230 A1* | 9/2009 | Pesetski et al. ............ 257/24 |

FOREIGN PATENT DOCUMENTS

| JP | 63-262875 A | 10/1988 |
| JP | 05-094954 A | 4/1993 |
| JP | 05094954 A * | 4/1993 |
| JP | 2006-220513 A | 8/2006 |
| JP | 2006-222279 A | 8/2006 |
| JP | 2008-010850 A | 1/2008 |
| JP | 2008-082987 A | 4/2008 |
| WO | 2006/103872 A | 10/2006 |
| WO | 2008/091273 A2 | 7/2008 |

* cited by examiner

*Primary Examiner* — Brook Kebede
(74) *Attorney, Agent, or Firm* — Kubotera & Associate LLC

(57) ABSTRACT

Disclosed is a carbon nanotube field effect transistor which stably exhibits excellent electrical conduction properties. Also disclosed are a method for manufacturing the carbon nanotube field effect transistor, and a biosensor comprising the carbon nanotube field effect transistor. First of all, an silicon oxide film is formed on a contact region of a silicon substrate by an LOCOS method. Next, an insulating film, which is thinner than the silicon oxide film on the contact region, is formed on a channel region of the silicon substrate. Then, after arranging a carbon nanotube, which forms a channel, on the silicon substrate, the carbon nanotube is covered with a protective film. Finally, a source electrode and a drain electrode are formed, and the source electrode and the drain electrode are electrically connected to the carbon nanotube, respectively. A field effect transistor manufactured by these processes stably exhibits excellent electrical conduction properties since the carbon nanotube, which serves as the channel, is not contaminated.

4 Claims, 16 Drawing Sheets

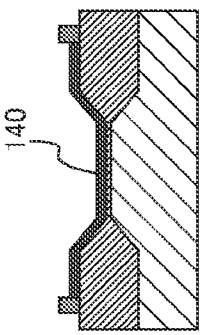
FIG.4A
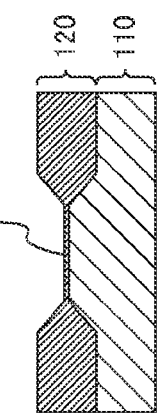
FIG.4B
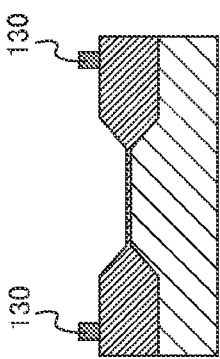
FIG.4C
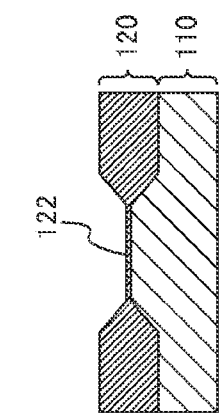
FIG.4D
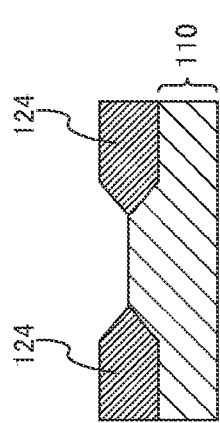
FIG.4E
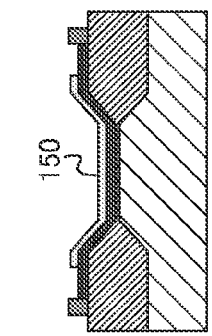
FIG.4F
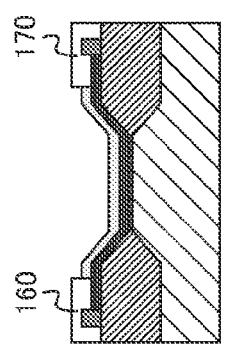
FIG.4G
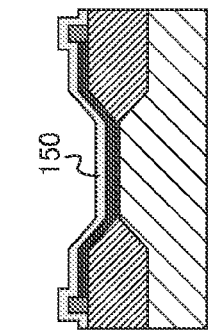

FIELD EFFECT TRANSISTOR, METHOD FOR MANUFACTURING THE SAME, AND BIOSENSOR

TECHNICAL FIELD

The present invention relates to a field-effect transistor using carbon nanotubes as a channel, and a method for manufacturing the same. The present invention also relates to a biosensor having the field effect transistor.

2. Background Art

A carbon nanotube (hereinafter simply referred to as a "CNT") is a tubular substance composed of carbon atoms and exhibits semiconducting or metallic properties depending on its chirality. CNTs are several nanometers in diameter and also can carry a high current density, making possible the formation of extremely narrow interconnection with one-dimensional conduction. Thus, CNTs hold a great promise for applications in quantum devices capable of high-speed operation. For example, research has been actively carried out into the use of CNTs exhibiting semiconducting properties as a channel of a field-effect transistor (hereinafter referred to as a "FET").

Currently, a field effect transistor in which CNTs are used as a channel (hereinafter referred to as a "CNT-FET") is manufactured by, for example, direct growth method in which CNTs are grown from a catalyst formed on a substrate followed by the formation of a source electrode and a drain electrode at either end of the CNTs, or dispersion method in which CNTs are dispersed on the substrate followed by the formation of a source electrode and a drain electrode at either end of the CNTs.

For example, Patent Literature 1 discloses an n-type CNT-FET using CNTs as a channel. In this technology, a CNT-FET is manufactured by forming a source electrode and a drain electrode at either end of CNTs grown from a catalyst, and forming a film of a nitrogen compound (e.g., silicon nitride) on the CNTs.

CITATION LIST

Patent Literature

PTL 1 Japanese Patent Application Laid-Open No. 2006-222279

SUMMARY OF INVENTION

Technical Problem

However, the above conventional manufacturing method has a drawback that a CNT-FET that stably exhibits excellent electrical conduction characteristics cannot be manufactured with good reproducibility.

In the above conventional manufacturing method, CNTs are exposed to a cleaning chemical, a resist used for patterning or other substance during the formation of a source electrode and a drain electrode, resulting in the formation of defects in the CNTs or contamination of the CNTs with resist residue. These defects lead to poor electrical conduction characteristics of the CNT-FET. Moreover, since CNTs with many defects tend to adsorb oxygen, water molecules and other substance from the surrounding environment, they also cause the hysteresis of CNT-FET together with contaminants that cannot be completely removed during the manufacturing process.

One possible approach to overcome the foregoing drawback is to form a protective film that covers CNTs prior to the formation of a source electrode and a drain electrode. In this case, as illustrated in FIG. 1, source electrode 40 and drain electrode 50 may contact CNT 30 through respective contact holes formed in protective film 60. This method, however, increases the likelihood that the contact holes entirely penetrate through gate oxide film 20 (silicon oxide film that covers one side of silicon substrate 10) and thus has suffered from limited ability to slim down gate oxide film 20 for improved CNT-FET characteristics.

It is therefore an object of the present invention to provide a method capable of manufacturing a CNT-FET that stably exhibits excellent characteristics with good reproducibility, a CNT-FET manufactured by the method, and a biosensor having the CNT-FET.

Solution to Problem

The inventors established that the foregoing problem can be solved by forming a protective film that covers a CNT prior to the formation of a source electrode and a drain electrode and thickening insulating films beneath the source electrode and drain electrode compared to the insulating film beneath the CNT. With additional studies, the inventors completed the present invention.

Namely, a first aspect of the present invention relates to CNT-FETs given below.

[1] A field effect transistor including:
   a silicon substrate;
   an insulating film covering one side of the silicon substrate;
   a source electrode and a drain electrode arranged on or over the insulating film;
   a channel formed of a carbon nanotube, the channel connecting the source electrode and the drain electrode; and
   a protective film covering the carbon nanotube,
   wherein a thickness of the insulating film in a region including the carbon nanotube is smaller than a thickness of the insulating film in a region including the source electrode and the drain electrode.

[2] The field effect transistor according to [1], wherein the insulating film in the region including the carbon nanotube and the protective film are made of high-permittivity material.

A second aspect of the present invention relates to methods of manufacturing a CNT-FET given below.

[3] A method of manufacturing a field effect transistor having a channel formed of a carbon nanotube, including:
   providing a silicon substrate;
   forming a silicon oxide film on the silicon substrate in a source electrode formation region and a drain electrode formation region by a LOCOS process;
   forming an insulating film on the silicon substrate in a carbon nanotube formation region, the insulating film being thinner than the silicon oxide film;
   providing a carbon nanotube on the insulating film;
   forming a protective film on the carbon nanotube; and
   forming a source electrode and a drain electrode on the silicon oxide film so that the source electrode and the drain electrode can be electrically connected to the carbon nanotube.

[4] The method according to [3], wherein the step of forming the source electrode and the drain electrode includes the steps of:
   forming contact holes in the protective film in the source electrode formation region and the drain electrode formation region, respectively, to expose a part of the carbon nanotube;

forming the source electrode on the protective film in the source electrode formation region so that the source electrode can be electrically connected to the carbon nanotube via the contact hole; and forming the drain electrode on the protective film in the drain electrode formation region so that the drain electrode can be electrically connected to the carbon nanotube via the contact hole A third aspect of the present invention relates to a biosensor given below.

[5] A biosensor including:

the field effect transistor according to [1] or [2]; and a target recognition molecule, wherein the target recognition molecule is immobilized either on the insulating film that covers one side of the silicon substrate or on a second insulating film that covers the other side of the silicon substrate, and a thickness of the insulating film or the second insulating film in a region in which the target recognition molecule is immobilized is smaller than a thickness of the insulating film or the second insulating film surrounding the region in which the target recognition molecule is immobilized.

Advantageous Effects of Invention

According to the present invention, it is possible to manufacture a CNT-FET that stably exhibits excellent characteristics with good reproducibility without having to use any special manufacturing apparatus. The present invention thus can realize high-yield mass production of CNT-FETs using an existing general manufacturing apparatus.

BRIEF DESCRIPTION OF DRAWINGS

FIGS. 4A to 4G are schematic views illustrating a method of manufacturing a CNT-FET according to Embodiment 1;

DESCRIPTION OF EMBODIMENTS

1. CNT-FET

Figure 1:
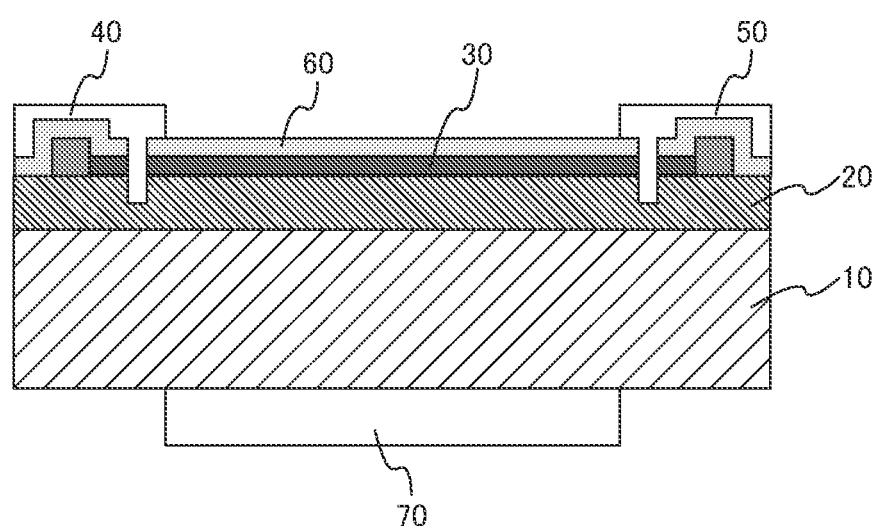
FIG. 1 is a sectional view illustrating a configuration of a CNT-FET.

A CNT-FET of the present invention includes a silicon substrate having an insulating film; a source electrode and a drain electrode which are arranged on or over the insulating film; one or more CNTs connecting the source electrode and the drain electrode; a protective film covering the CNTs; and a gate electrode. A main feature of the CNT-FET of the present invention is that (1) an insulating film arranged in a region including one or more CNTs that serve as a channel (hereinafter also referred to as a "channel region") is thinner than an insulating film arranged in regions including a source electrode and a drain electrode, respectively (hereinafter also referred to as "contact regions"), and that (2) the CNTs that serve as a channel are covered with a protective film.

[Substrate]

A substrate used for the CNT-FET of the present invention is a silicon substrate, which is covered with an insulating film on at least one side where a source electrode, a drain electrode and CNT are arranged.

There is no particular limitation on the size and thickness of the silicon substrate. Also, there is no particular limitation on the material of the insulating film as long as it has insulating properties and high permittivity. Examples of materials of the insulating film include inorganic compounds such as silicon oxide, silicon nitride, aluminum oxide, hafnium oxide, zirconium oxide and titanium oxide, and organic compounds such as acrylic resins and polyimides. In a case where the CNT-FET of the present invention is of the back-gate type, for the purpose of reducing gate voltage, the material for the insulating film in the channel region (gate insulating film) is preferably chosen from high-permittivity materials such as silicon nitride, aluminum oxide, hafnium oxide, zirconium oxide and titanium oxide. The insulating film may have a single layer structure (see FIG. 2), a multilayered structure (see FIG. 6B), or a partially multilayered structure (see FIG. 6A).

One feature of the CNT-FET of the present invention is that an insulating film in the channel region is thinner than the insulating film in the contact regions. The insulating film in the channel region is preferably made as thin as possible as long as its insulating property can be ensured; the thickness may be appropriately determined depending on the material of the insulating film. For example, when the insulating film in the channel region is formed of a single-layered silicon oxide film, the silicon oxide may be of the order of 2 nm to 500 nm in thickness. On the other hand, when the insulating film in the channel region is formed of a single-layer high-permittivity insulating film (film made of high-permittivity material), the thickness may be of the order of 2 nm to 100 nm.

Preferably, the insulating film in the contact regions is sufficiently thicker than that in the channel region. This is to enhance trans-conductance by effectively forming an electric field in the CNTs that serve as a channel. For example, the insulating film in the contact regions may be of the order of 200 nm to 1,000 nm in thickness. The silicon substrate may be covered by the insulating film only on one side (surface where a source electrode and a drain electrode are arranged), or on both sides.

[Channel]

The channel connecting a source electrode and a drain electrode are composed of CNT. Either a single-walled CNT or a multi-walled CNT may be employed, but single-walled CNT is preferable. The source electrode and drain electrode may be connected by one or multiple CNTs. For example, the source electrode and drain electrode may be connected by multiple CNTs lying over one another or by CNT bundles.

[Protective Film]

Another feature of the CNT-FET of the present invention is that the CNT that serves as a channel is covered with a protective film. There is no particular limitation on the material of the protective film as long as it has insulating properties. Examples of materials of the insulating protective film include silicon oxide, silicon nitride, aluminum oxide, hafnium oxide, zirconium oxide and titanium oxide. In a case where the CNT-FET of the present invention is of the top-gate type, for the purpose of reducing gate voltage, the material of the protective film (gate insulating film) is preferably chosen from high-permittivity materials such as silicon nitride, aluminum oxide, hafnium oxide, zirconium oxide and titanium oxide. The protective film may be formed only around the CNT, or may be formed so as to entirely or partially cover the surface of the substrate on which the CNT is to be arranged. There is no particular limitation on the thickness of the protective film as long as it is capable of completely covering (protecting) the CNT that forms a channel; a thickness of the order of 50 nm to 100 nm (e.g., 20 nm) suffices.

[Source Electrode and Drain Electrode]

A source electrode and a drain electrode are arranged on or over the insulating film of the silicon substrate. The source electrode and drain electrode may be formed directly on the insulating film or on the protective film formed on the insulating film. When the source electrode and drain electrode are formed on the protective film, they are connected to the CNT via respective contact holes formed in the protective film (see FIGS. 8A and 8B).

There is no particular limitation on the material of the source electrode and drain electrode as long as it is electrically conductive. Examples of materials of the source electrode and drain electrode include metals such as gold, platinum, chromium, titanium, aluminum, palladium and molybdenum, and semiconductors such as polysilicon. The source electrode and drain electrode may have a multilayered structure comprising two or more different metals, such as a structure in which a layer of gold is laminated on a layer of titanium, for example. There is no particular limitation on the shape of the source electrode and drain electrode and on the distance between the electrodes. The source electrode and drain electrode are electrically connected to the CNT that serves as a channel. The source electrode and drain electrode may be connected only to a side surface of the CNT (side-contact structure: see FIG. 2), may be connected only to an end surface (cut surface) of the CNT (end-contact structure: see FIG. 8A), or may be connected to both an end surface and its surrounding side surface of the CNT (see FIG. 8B).

[Gate Electrode]

A CNT-FET of the present invention has a gate electrode. There is no particular limitation on the material of the gate electrode as long as it is electrically conductive. Examples of materials of the gate electrode include metals such as gold, platinum, chromium, titanium, brass and aluminum. The gate electrode is formed, for example, by vapor deposition of any of these metals at any desired position. Alternatively, a separately prepared electrode (e.g., a gold thin film) may be arranged at any desired position for use as the gate electrode. There is no particular limitation on the position at which the gate electrode is arranged, as long as a current that flows between the source electrode and drain electrode (source-drain current) can be controlled by the gate voltage. For example, the CNT-FET of the present invention can employ a top-gate type, side-gate type, or back-gate type mode according to the position of the gate electrode.

As described above, since the CNT-FET of the present invention is configured to prevent the CNT from adsorbing water molecules and the like by covering the CNT with a protective film, it is possible to reduce the hysteresis in the CNT-FET. Moreover, since the insulating film in the channel region is made thin in the CNT-FET of the present invention, it is possible to improve trans-conductance, especially where the CNT-FET is of the back-gate type.

The CNT-FET of the present invention is preferably manufactured using a manufacturing method of the present invention described below. The reason for this is that the manufacturing method of the present invention can manufacture a CNT-FET having excellent electrical conduction characteristics by forming a source electrode and a drain electrode without exposing the CNT to a cleaning chemical or resist.

2. Method of Manufacturing CNT-FET

A feature of the method of the present invention for manufacturing a CNT-FET is that (1) a silicon oxide film is formed on a silicon substrate in the contact regions by the LOCOS process, and an insulating film, which is thinner than the silicon oxide film, is formed on the silicon substrate in the channel region, and that (2) after providing one or more CNTs on the insulating film in the channel region and before forming a source electrode and a drain electrode in the contact regions, a protective film for covering the CNTs is formed. The step of providing the CNT and the step of forming the gate electrode can be carried out employing techniques known in the art as appropriate.

[Provision of Substrate]

First, a silicon substrate is provided. There is no particular limitation on the size and thickness of the silicon substrate.

By the LOCOS process, a silicon oxide film is formed on the silicon substrate in the contact regions (regions where a source electrode and a drain electrode is to be formed, respectively). Preferably, the silicon oxide film is sufficiently thicker than the insulating film in the channel region. For example, the silicon oxide film in the contact regions may be of the order of 200 nm to 1,000 nm.

After forming the silicon oxide film in the contact regions, an insulating film is formed on the silicon substrate in the channel region (a region where one or more CNTs are to be arranged). In the case of a back-gate type or side-gate type FET, this insulating film serves as a gate insulating film. There is no particular limitation on the material of the insulating film as long as it has insulating properties and high permittivity.

The insulating film may have a single layer structure, a multilayered structure, or a partially multilayered structure. The insulating film in the contact region may be formed at the same time as the insulating film in the channel regions (see FIGS. 7A to 7G). There is no particular limitation on the thickness of the insulating film in the channel region as long as it is thinner than the silicon oxide film in the contact regions; however, the insulating film in the channel region is preferably made as thin as possible, and the thickness may be appropriately determined depending on the material of the insulating film. For example, when the insulating film in the channel region is formed of a single-layered silicon oxide film, the thickness of the silicon oxide film may be of the order of 2 nm to 500 nm. On the other hand, when the insulating film in the channel region is formed of a single-layered high-permittivity insulating film (film made of high-permittivity material), the thickness may be of the order of 2 nm to 100 nm.

[Arrangement of CNT]

One or more CNTs, which serve as a channel, are arranged on the insulating film in the channel region, and a method of arranging the CNTs may be appropriately selected from those known in the art, such as direct growth method and dispersion method. For example, a catalyst layer for growing CNTs is formed on the silicon oxide film (or the insulating film formed thereon) in the contact regions, and then CNTs are grown by means of CVD in such a way that they connect the contact regions.

[Formation of Protective Film]

After arranging the CNTs and before forming the source electrode and a drain electrode, the CNTs are covered by a protective film. There is no particular limitation on the method of forming the protective film; however, a method that causes little thermal damage or chemical damage to the CNTs is desirable. Examples of such a method include catalytic CVD and atomic layer deposition (ALD), which do not use plasma and require a low reaction temperature. By ALD, water molecules adsorbed to the CNTs can be removed in the film formation process, thus reducing the hysteresis of the CNT-FET. Moreover, with ALD, the protective film is composed of thin monoatomic layers formed one at a time in a sequential manner. Thus, ALD can form a protective film that has good film uniformity and step coverage and thus covers not only the upper surface of the CNTs but wraps around and covers the lower surface as well.

There is no particular limitation on the material of the protective film as long as it has insulating properties. There is no particular limitation on the thickness of the protective film as long as it is sufficient to completely cover (protect) the CNTs forming the channel; a thickness of the order of 50 nm to 100 nm (e.g., 20 nm) suffices.

As noted above, a feature of the manufacturing method of the present invention is that the CNTs that serve as a channel are covered with an insulating protective film before proceeding to a process for forming a source electrode and a drain electrode. Therefore, the CNTs that serve as a channel are protected both physically and chemically in subsequent manufacturing processes. This protective film can also function as a final protective film of an FET device.

[Formation of Source Electrode and Drain Electrode]

After forming a protective film covering the CNTs, a source electrode and a drain electrode are formed in the respective contact regions. At this time, the source electrode and drain electrode are formed so that they can be electrically connected to the CNTs. For example, after exposing the CNTs by entire or partial removal of the protective film in the contact regions, the source electrode and drain electrode may be formed so as to contact the region in which the CNTs are exposed.

Figure 2:
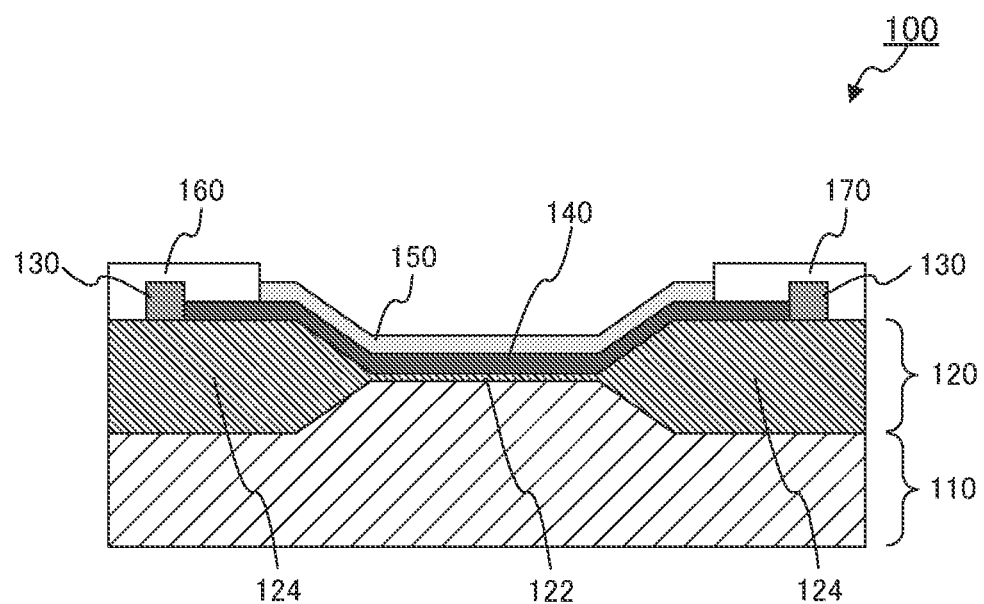
FIG. 2 is a sectional view illustrating a configuration of a CNT-FET according to Embodiment 1.

At this time, areas of the protective film corresponding to electrode formation regions are exclusively removed by wet etching or other method so that the CNTs are exposed on their side surface, whereby a source drain and a drain electrode can be connected only to the side surface of the CNTs (side-contact structure; see FIG. 2). Alternatively, the protective film and CNTs are partly removed by dry etching or other method so that the CNTs are exposed on their end surface (cut surface), whereby a source electrode and a drain electrode can be connected only to the end surface of the CNTs (end-contact structure; see FIG. 8A). Moreover, after exposing the end surface (cut surface) of the CNTs, areas of the protective film around the end surface of the CNTs are removed by wet etching or other method so that the end surface and its surrounding side surface are exposed, whereby a source electrode and a drain electrode can be connected to the end surface and its surrounding side surface of the CNTs (see FIG. 8B).

There is no particular limitation on the method of arranging the source electrode and drain electrode; a method known in the art can be appropriately employed. For example, a metal film or the like may be patterned by photolithography. There is no particular limitation on the material of the source electrode and drain electrode as long as it is electrically conductive. The source electrode and drain electrode may have a multilayered structure comprising two or more different metals, such as a structure in which a layer of gold is laminated on a layer of titanium, for example.

[Arrangement of Gate Electrode]

There is no particular limitation on the method of arranging a gate electrode; a method known in the art can be appropriately employed. For example, a metal film or the like may be patterned by photolithography, as in the case of the source electrode and drain electrode. Also, when a separately prepared electrode is used as a gate electrode, that electrode can be arranged at a desired position.

In the manufacturing method of the present invention, the formation of a source electrode and a drain electrode on a substrate is preceded by the formation of a protective film for covering CNTs. It is thus possible to reduce CNT defects and CNT contamination with resist residue during the manufacturing process. A clean CNT channel created in this way exploits the one-dimensional conductivity of CNTs to the maximum, and exhibits better FET characteristics than conventional ones. Moreover, since the CNTs are prevented from adsorbing water molecules and the like by means of a protective film in the CNT-FET of the present invention thus manufactured, it is possible to reduce the hysteresis of the CNT-FET.

The manufacturing method of the present invention also has an advantage that even when contact holes are formed in the protective film, an insulating film (silicon oxide film) is made thick in the contact regions and therefore the contact holes are less likely to entirely penetrate through that insulating film. Moreover, with the manufacturing method of the present invention, an insulating film in the channel region can be made thin as the insulating film in the contact regions is selectively made thick.

Thus, with the manufacturing method of the present invention, it is possible to manufacture a CNT-FET of the present invention that stably exhibit excellent electrical conductivity with good reproducibility without having to use any special apparatus.

3. Biosensor

A biosensor of the present invention includes a CNT-FET of the present invention and target recognition molecules.

There is no particular limitations on the target recognition molecules as long as a substance that may specifically react with a substance to be detected (target substance) is employed. Examples of target recognition molecules include proteins such as antibodies, enzymes and lectin, nucleic acid, oligosaccharides or polysaccharides, and substances having the structure of the foregoing.

Target recognition molecules are preferably immobilized on an insulating film that covers a silicon substrate of the CNT-FET of the present invention. Hereinafter, a region in which target recognition molecules are immobilized is referred to as a "reaction region." The insulating film in the reaction region may be the same insulating film as that on which the CNTs, source electrode are drain electrode are arranged, or may be a different insulating film (e.g., a second insulating film that covers an opposite side of the silicon substrate).

The insulating film in the reaction region is preferably thinner than the surrounding insulating film. That is, the reaction region is preferably shaped in a concave shape (see FIG. 12). This configuration not only allows a sample solution to be held within the reaction region, but also allows electrical flux lines emitted from the gate electrode toward the substrate surface to efficiently pass through the reaction region. This configuration also prevents the target recognition molecules and gate electrode from coming in direct contact with each other even when the gate electrode is positioned overlapping the reaction region in which the target recognition molecules are immobilized. By way of example, by forming a thick silicon oxide film around the reaction region by the LOCOS process, it is possible to control the positional relationship or interval between the gate electrode and target recognition molecules.

There is no particular limitation on the thickness of the insulating film in the reaction region; the thickness may be of the order of 1 nm to 200 nm. The insulating film needs to be provided in the reaction region for immobilization of target recognition molecules thereon, but the insulating film is not necessarily required to be electrically insulating. Accordingly, the insulating film in the reaction region may be a chemically oxidized film or naturally oxidized film of the order of 1 nm in thickness.

There is no particular limitation on the shape and size (area) of the reaction region; they may be appropriately determined depending on the volume of a sample solution to be fed and on the shape of the gate electrode. For example, when the reaction region is square, each side may be several millimeters (e.g., 5 mm) in length.

Detection of a target substance by means of the biosensor of the present invention may be accomplished by feeding a sample solution containing a detection target to the reaction region, applying voltage to the gate electrode, and measuring changes in electrical characteristics (e.g., $I_{ds}$-$V_g$ characteristics) between the source electrode and drain electrode. Alternatively, detection of a target substance may be accomplished by measuring changes in electrical characteristics between the source electrode and drain electrode after drying the sample solution.

The biosensor of the present invention includes the CNT-FET of the present invention that stably exhibits excellent electrical characteristics, and thus is capable of stable high-precision target detection.

Hereinafter, with reference to the accompanying drawings, embodiments of the present invention will be described, which however shall not be construed as limiting the scope of the invention thereto.

(Embodiment 1)

Embodiment 1 is directed to a CNT-FET constructed as a side-contact structure and in which an insulating film in the channel region is formed of a single-layered silicon oxide film.

FIG. 2 is a sectional view illustrating a configuration of a CNT-FET according to Embodiment 1 of the present invention. In FIG. 2, CNT-FET 100 includes silicon substrate 110, insulating film 120, catalyst layer 130, CNT 140, protective film 150, source electrode 160, drain electrode 170, and gate electrode 180 (not illustrated). Insulating film 120 includes a thin insulating film (gate insulating film) in the channel region and thick insulating films in the contact regions. In this CNT-FET 100, a current that flows between source electrode 160 and drain electrode 170 is controlled by the voltage applied to gate electrode 180 (not illustrated).

Silicon substrate 110 is covered with insulating film 120 on at least one side. The insulating film in the channel region is formed of thin single-layered silicon oxide film 122 (thickness: 2 nm to 500 nm), and the insulating film in the contact regions is formed of a thick single-layered silicon oxide film 124 (thickness: 200 nm to 1,000 nm).

CNT 140 is arranged on insulating film 120. CNT 140 is electrically connected to source electrode 160 and drain electrode 170 and serves as a channel. As will be described later, CNT 140 according to this embodiment is formed by chemical vapor deposition and, therefore, contacts catalyst layer 130 arranged on insulating film 120. Source electrode 160 and drain electrode 170 may be connected by one CNT 140 as illustrated in FIG. 2, or may be connected by multiple CNTs.

Protective film 150 is an insulating film that covers CNT 40 except for regions where source electrode 160 and drain electrode 170 contact CNT 140. Protective film 150 is, for example, a hafnium oxide film (thickness: 2 nm to 100 nm).

Source electrode 160 and drain electrode 170 are arranged on silicon oxide films 124 in the respective contact regions. Source electrode 160 and drain electrode 170 contact a side surface of CNT 140 (side-contact structure).

Figure 3A:
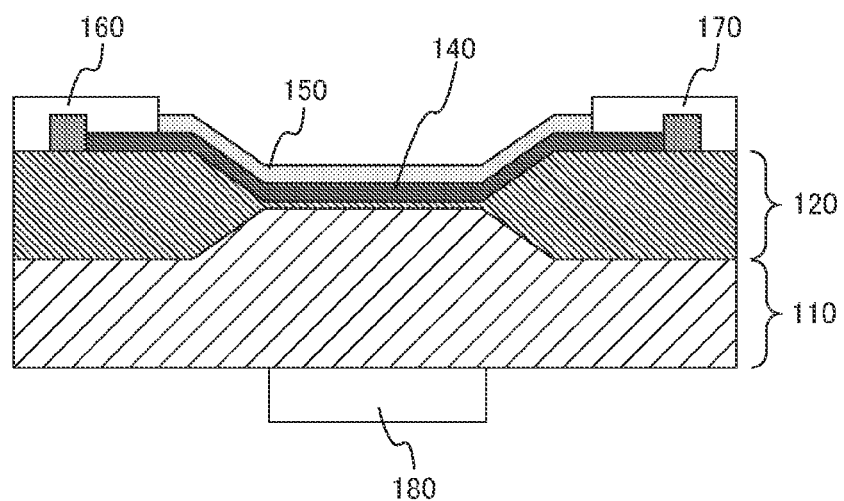
FIGS. 3A to 3C are sectional views illustrating different types of a CNT-FET according to Embodiment 1.
Figure 3B:
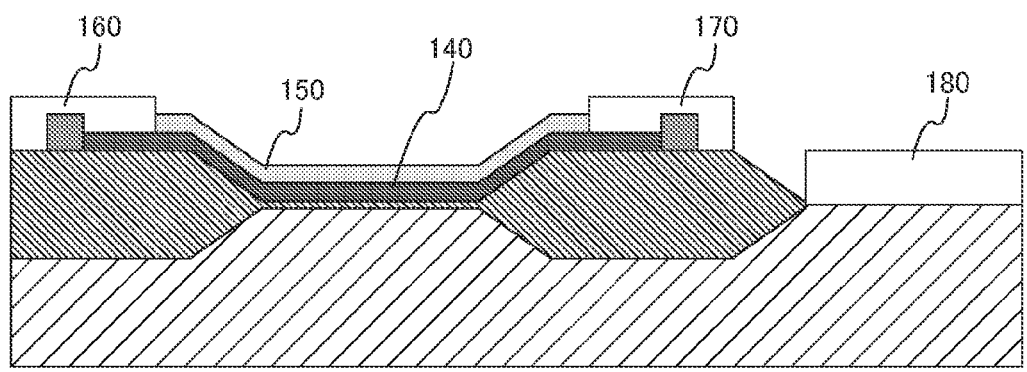
Figure 3C:
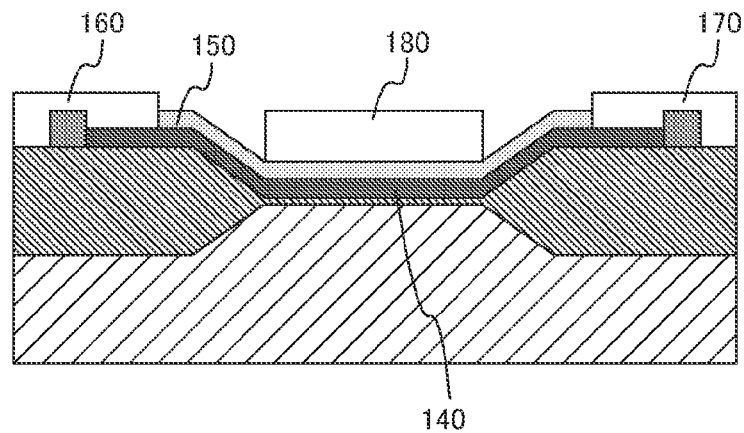

Gate electrode 180 is arranged at such a position that a current that flows between source electrode 160 and drain electrode 170 (source-drain current) can be controlled. As illustrated in FIGS. 3A to 3C, CNT-FET 100 according to this embodiment can employ a top-gate type (FIG. 3A), side-gate type (FIG. 3B), or top-gate type (FIG. 3C) mode according to the position of gate electrode 180.

Since the insulating film in the channel region is made thin whereas the insulating films in the contact regions are made thick in CNT-FET according to this embodiment, the CNT-FET can effectively form an electric field exclusively in the channel (CNT). Thus, the CNT-FET according to this embodiment exhibits excellent trans-conductance.

Moreover, the CNT-FET according to this embodiment can reduce the hysteresis since the CNTs are prevented from adsorbing water molecules and the like by means of a protective film.

Next, a method of manufacturing the CNT-FET 100 according to this embodiment will be described with references to the schematic illustrations of FIG. 4A to FIG. 5E.

First, as illustrated in FIG. 4A, a surface of silicon substrate 110 is partly oxidized to form thick silicon oxide film 124 on silicon substrate 110 in the contact regions (LOCOS process).

An example of the procedure of the LOCOS process is described with reference to the schematic illustrations of FIGS. 5A to 5E.

Figure 5A:
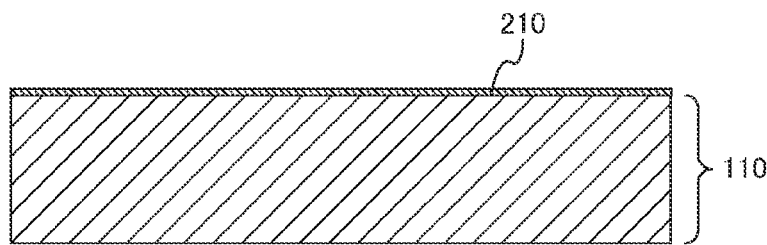
FIGS. 5A to 5E are schematic views for explaining the LOCOS process.
Figure 5B:
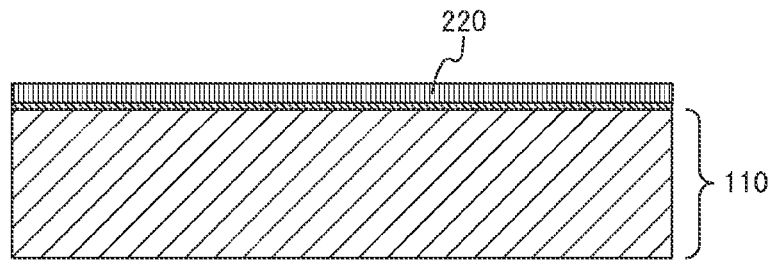
Figure 5C:
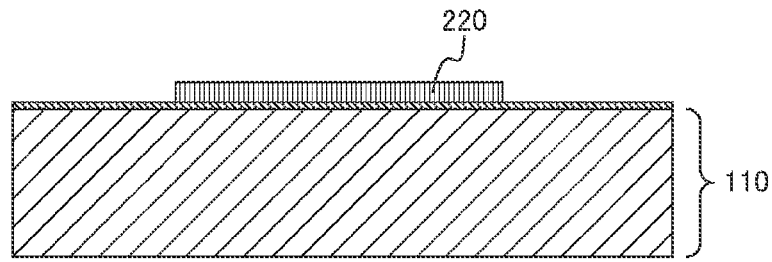
Figure 5D:
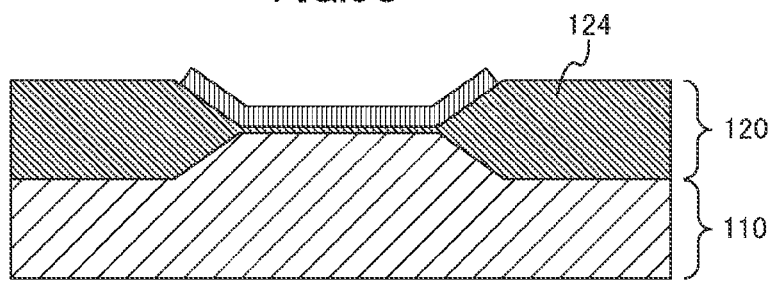
Figure 5E:
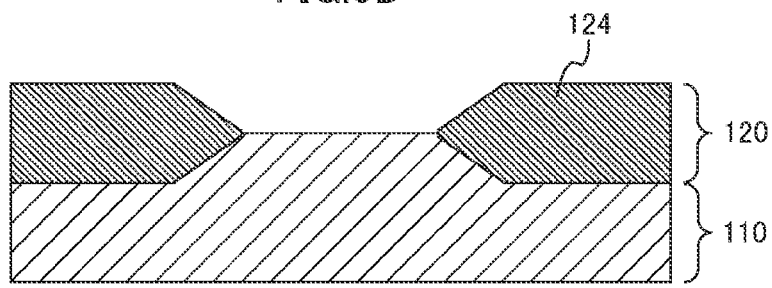

First, silicon oxide film 210 is formed on silicon substrate 110 by thermal oxidization or other method (see FIG. 5A), and then silicon nitride film 220 is formed on silicon oxide film 210 by CVD or other method (see FIG. 5B). Silicon oxide film 210 is provided in order to protect silicon substrate 110. Subsequently, areas of silicon nitride film 220 corresponding to contact regions are etched away (see FIG. 5C). The region from which silicon nitride has been removed is a region where thick silicon oxide film 124 is to be formed.

Wet oxidizing treatment is then carried out at around 1,000° C. Because silicon nitride film 220 is not oxidized, the region in which the silicon oxide film is exposed (regions from which silicon nitride film 220 is removed) is selectively oxidized (see FIG. 5D). At this point, a part of thick silicon oxide film 124 extends under silicon nitride film 220 to form the so-called "bird's beak." After oxidizing treatment, silicon nitride film 220 and silicon oxide film 210 in the channel region are removed, completing the formation of silicon oxide film 124 in the contact regions (see FIG. 5E).

The explanation now goes back to the method of manufacturing CNT-FET 100. As illustrated in FIG. 4B, thin silicon oxide film 122 is formed in the channel region. For example, thin silicon oxide film 122 may be formed in the channel region by heating silicon substrate 110 in ambient atmosphere.

Next, as illustrated in FIG. 4C, catalyst layer 130 for growing CNT 40 is formed on silicon oxide film 124 in the contact regions. For example, catalyst layer 130 can be formed by sequentially depositing a thin silicon film, a thin aluminum film, a thin iron film, and a thin molybdenum film by sputtering, followed by etching.

Next, as illustrated in FIG. 4D, CNT 140 is grown from catalyst layer 130. There is no particular limitation on the method of growing CNT 140; for example, low-pressure CVD may be employed. At this time, catalyst layers 130 are preferably bridged by one or more CNTs 140.

Next, as illustrated in FIG. 4E, protective film 150 is formed in such a way as to cover CNT 140 thus grown. For example, protective film 150 made of hafnium oxide or silicon nitride may be formed by catalytic CVD on silicon substrate 110 on which CNT 140 has been grown.

Next, as illustrated in FIG. 4F, areas of protective film 150 where source electrode 160 and drain electrode 170 are to be formed are removed, exposing side surfaces of CNT 140. For example, protective film 150 is masked with a resist film except for a surface where source electrode 160 and drain electrode 170 are to be formed, after which wet etching is performed with an etchant containing hydrofluric acid. Wet etching etches away areas of protective film 150 not covered with the resist film, exposing side surfaces of CNT 140 and silicon oxide film 124 underneath the etched-away areas.

Next, as illustrated in FIG. 4G, source electrode 160 and drain electrode 170 are arranged on insulating film 124 in the respective contact regions so that they electrically contact CNT 140. For example, source electrode 160 and drain electrode 170 can be formed by depositing a thin aluminum film on insulating film 124 in the contact regions and on protective film 150 by sputtering, and etching away the thin aluminum film deposited on protective film 150. In an example illustrated in FIG. 4G, since source electrode 160 and drain electrode 170 are formed in a state where side surfaces of CNT 140 are exposed (see FIG. 4F), source electrode 160 and drain electrode 170 are connected only to the side surfaces of CNT 140 (side-contact structure).

Finally, gate electrode 180 is formed at a desired position (see FIGS. 3A to 3C). For example, gate electrode 180 can be formed by forming a thin aluminum film at a desired position by sputtering and, where necessary, etching the aluminum film.

As described above, since the manufacturing method of this embodiment forms protective film 150 before proceeding to the step of forming source electrode 160 and drain electrode 170, it is possible to physically and chemically protect CNT 140 in the step of forming source electrode 160 and drain electrode 170. As a result, the manufacturing method of this embodiment can manufacture a CNT-FET that has a clean CNT channel and while exploiting the one-dimensional conductivity of CNT to the maximum.

(Embodiment 2)

Embodiment 2 is directed to a CNT-FET constructed as a side-contact structure and in which an insulating film in the channel region includes a high-permittivity insulating film. The same components as those of the CNT-FET according to Embodiment 1 are given the same reference signs and duplicate description is omitted.

Figure 6A:
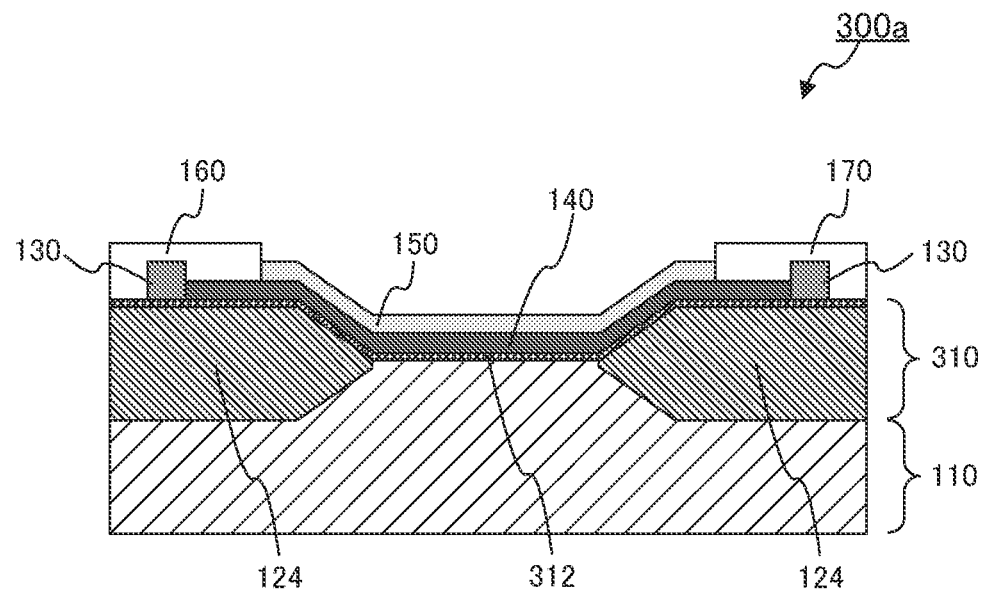
FIGS. 6A and 6B are sectional views illustrating configurations of a CNT-FET according to Embodiment 2.
Figure 6B:
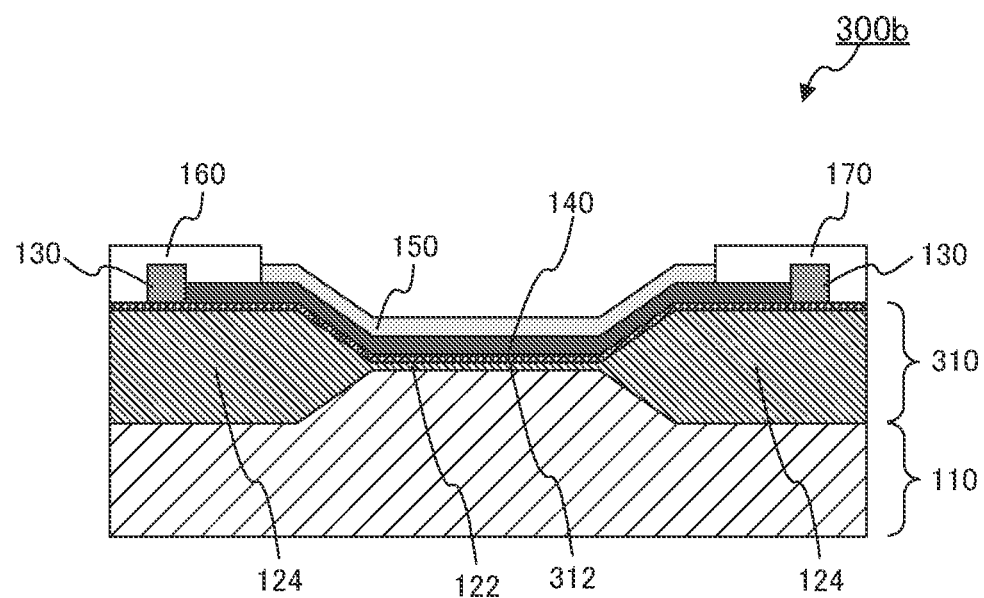

FIGS. 6A and 6B are sectional views illustrating configurations of a CNT-FET according to Embodiment 2. In FIGS. 6A and 6B, CNT-FET 300 includes silicon substrate 110, insulating film 310, catalyst layer 130, CNT 140, protective film 150, source electrode 160, drain electrode 170, and gate electrode 180 (not illustrated). Components other than insulating film 310 are identical to the respective components of the CNT-FET according to Embodiment 1.

Insulating film 310 includes a thin insulating film in the channel region and thick insulating films in the contact regions. The insulating film in the channel regions is formed of a thin high-permittivity insulating film 312 (see FIG. 6A), or formed of a thin high-permittivity insulating film 312 and of a thin silicon oxide film 122 (see FIG. 6B). The insulating film in the contact region is formed of a thick silicon oxide film 124 and of a thin high-permittivity insulating film 312.

With reference to the illustrations of FIGS. 7A to 7G, a method of manufacturing CNT-FET 300a according to this embodiment (a CNT-FET in which an insulating film in the channel region is formed of a thin high-permittivity insulating film; see FIG. 6A) will be described below. Steps other than the step of forming high-permittivity insulating film 312 are identical to the respective steps in the method of manufacturing CNT-FET 100 according to Embodiment 1.

Figure 7A:
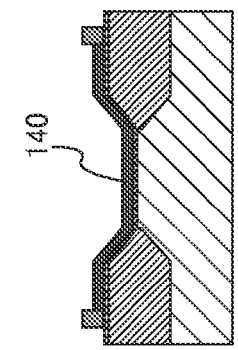
FIGS. 7A to 7G are schematic views illustrating a method of manufacturing a CNT-FET according to Embodiment 2.
Figure 7B:
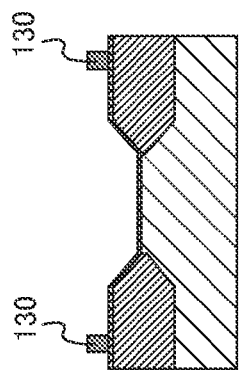
Figure 7C:
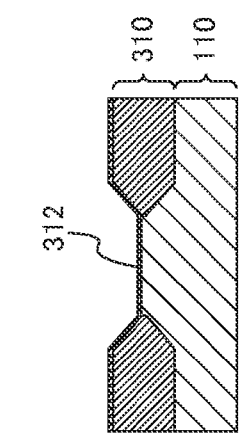
Figure 7D:
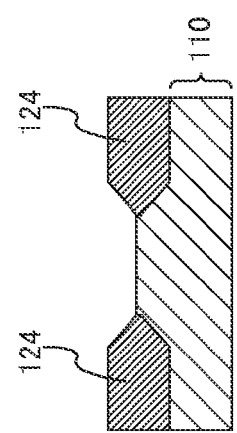
Figure 7E:
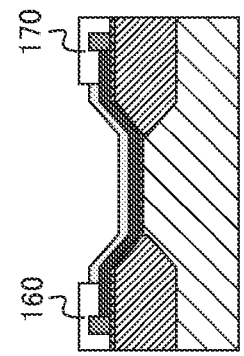
Figure 7F:
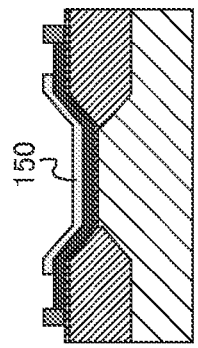
Figure 7G:
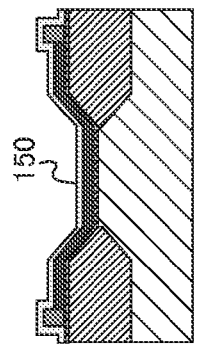

First, thick silicon oxide film 124 is formed on silicon substrate 110 in contact regions (see FIG. 7A). Next, high-permittivity insulating film 312 is formed on silicon substrate 110 (see FIG. 7B). For example, high-permittivity insulating film 312 made of hafnium oxide or the like may be formed on silicon substrate 110 by catalytic CVD. Next, catalyst layer 130 for growing CNT 140 is formed on high-permittivity insulating film 312 in the contact regions (see FIG. 7C). CNT 140 is then grown from catalyst layers 130 (see FIG. 7D). Protective film 150 is formed in such a way as to cover CNT 140 (see FIG. 7E). Next, areas of protective film 150 where source electrode 160 and drain electrode 170 are to be formed are removed, exposing side surfaces of CNT 140. Next, source electrode 160 and drain electrode 170 are arranged on insulating films 124 in the respective contact regions so that they electrically contact CNT 140 (see FIG. 7G). Finally, gate electrode 180 is formed at a desired position.

Furthermore, in the procedure described above, by forming thin silicon oxide film 122 in the channel region before the step of forming high-permittivity insulating film 312 (see FIG. 7B), it is possible to manufacture CNT-FET 300b according to this embodiment (a CNT-FET in which an insulating film in the channel region is formed of a thin high-permittivity insulating film and of a thin silicon oxide film; see FIG. 6B).

Thus, since the insulating film in the channel region of the CNT-FET according to this embodiment includes a high-permittivity insulating film, the insulating film in the channel region can be made thinner while ensuring the effects of the CNT-FET according to Embodiment 1. Thus, the CNT-FET according to this embodiment exhibits excellent trans-conductance.

(Embodiment 3)

Embodiment 3 is directed to a CNT-FET constructed as an end-contact structure and in which an insulating film in the channel region is formed of a silicon oxide film. The same components as those of the CNT-FET according to Embodiment 1 are given the same reference signs and duplicate description is omitted.

Figure 8A:
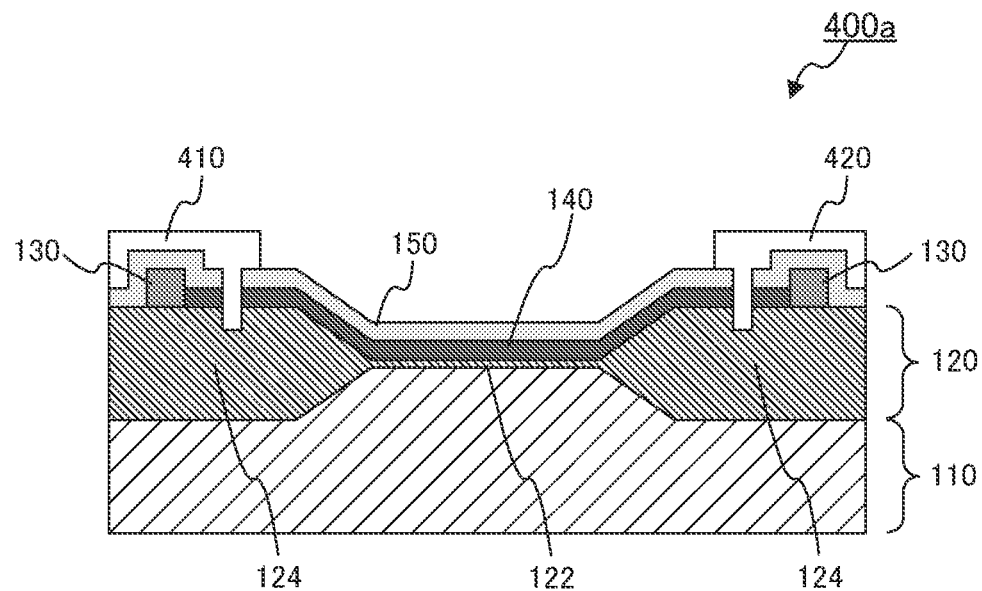
FIGS. 8A and 8B are sectional views illustrating configurations of a CNT-FET according to Embodiment 3.
Figure 8B:
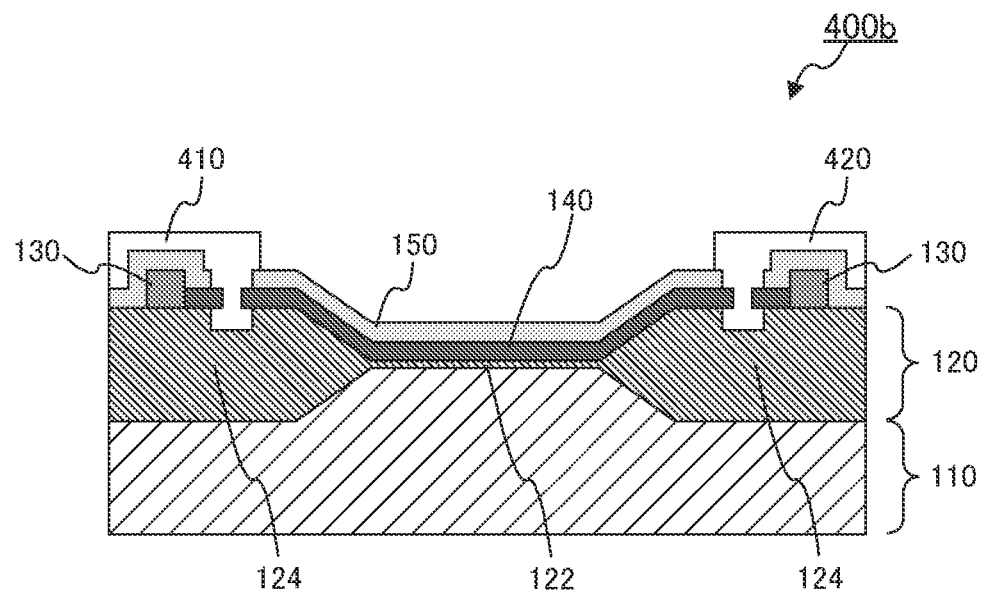

FIGS. 8A and 8B are sectional views illustrating configurations of a CNT-FET according to Embodiment 3. In FIGS. 8A and 8B, CNT-FET 400 includes silicon substrate 110, insulating film 120, catalyst layer 130, CNT 140, protective film 150, source electrode 410, drain electrode 420, and gate electrode 180 (not illustrated). Components other than source electrode 410 and drain electrode 420 are identical to the respective components of the CNT-FET according to Embodiment 1.

Source electrode 410 and drain electrode 420 are arranged on protective film 150 in the respective contact regions. Source electrode 410 and drain electrode 420 are connected to an end surface of CNT 140 via respective contact holes formed in protective film 150. Source electrode 410 and drain electrode 420 may be connected only to an end surface of CNT 140 (end-contact structure: see FIG. 8A), or may be connected to both an end surface and its surrounding side surface of CNT 140 (see FIG. 8B).

With reference to the illustrations of FIGS. 9A to 9G, a method of manufacturing CNT-FET 400a according to this embodiment (a CNT-FET constructed as an end-contact structure) will be described below. Steps other than the step of forming contact holes and the step of forming source electrode 410 and drain electrode 420 are identical to the respective steps in the method of manufacturing CNT-FET 100 according to Embodiment 1.

Figure 9D:
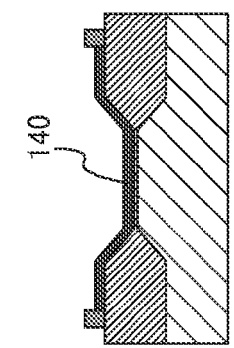
FIGS. 9A to 9G are schematic views illustrating a method of manufacturing a CNT-FET according to Embodiment 3.
Figure 9C:
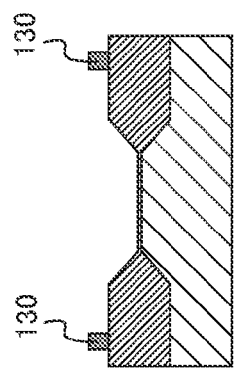
Figure 9B:
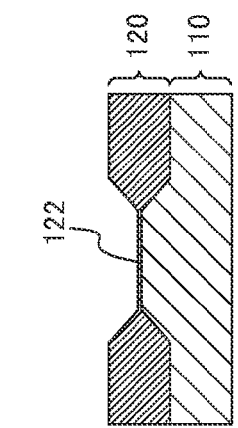
Figure 9A:
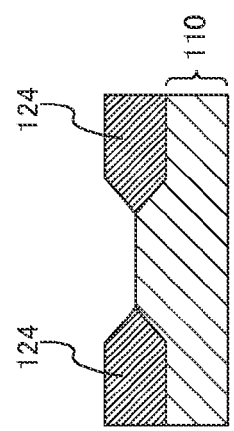

First, thick silicon oxide film 124 is formed on silicon substrate 110 in the contact regions (see FIG. 9A). Next, thin silicon oxide film 122 is formed on the channel region (see FIG. 9B). Next, catalyst layer 130 for growing CNT 140 is formed on silicon oxide film 124 in the contact regions (see FIG. 9C). CNT 140 is then grown from catalyst layers 130 (see FIG. 9D). Protective film 150 is formed in such a way as to cover CNT 140 (see FIG. 9E).

Figure 9G:
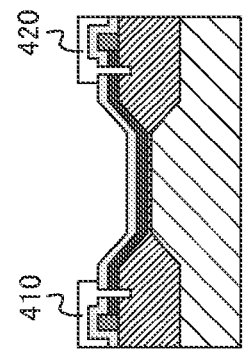
Figure 9F:
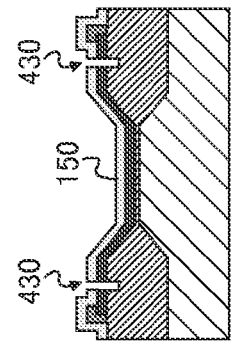
Figure 9E:
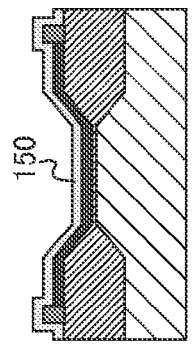

Next, contact holes 430 that extend substantially perpendicularly to the substrate surface are formed in the protective film 150 in the respective contact regions, exposing end surfaces of CNT 140 (see FIG. 9F). This may be accomplished by, for example, masking areas of protective film 150 other than areas where contact holes 430 are to be formed with a resist film and removing the unmasked areas by dry etching. At this point, since silicon oxide film 124 in the contact regions is made thick, it is possible to prevent contact holes 430 from reaching as far as silicon substrate 110. By performing dry etching in this way, areas of protective film 150 not masked with the resist mask and areas of CNT 140 beneath the unmasked areas are removed, thus exposing end surfaces (cut surfaces) of CNT 140.

Next, source electrode 410 and drain electrode 420 are formed on protective film 150 in the respective contact regions so that they are electrically connected to the end surfaces of CNT 140 via respective contact holes 430 (see FIG. 9G). Finally, gate electrode 180 is formed at a desired position.

Furthermore, in the procedure described above, by performing wet etching before the step of forming source electrode 410 and drain electrode 420 (see FIG. 9G), it is possible to manufacture CNT-FET 400b according to this embodiment (a CNT-FET in which a source electrode and a drain electrode contact an end surface and a side surface in the vicinity of the end surface of the CNT; see FIG. 8B).

Thus, since the contact area between the source electrode and CNT is substantially equal to the contact area between the drain electrode and CNT, the CNT-FET of this embodiment exhibits highly symmetrical electrical characteristics while providing the effects of the CNT-FET according to Embodiment 1. Namely, the CNT-FET according to this embodiment exhibits electrical characteristics that are independent from the polarity of voltage to be applied to the source electrode and drain electrode.

(Embodiment 4)

Embodiment 4 is directed to a CNT-FET constructed as an end-contact structure and in which an insulating film in the channel region includes a high-permittivity insulating film. The same components as those of the CNT-FETs according to Embodiments 1 to 3 are given the same reference signs and duplicate description is omitted.

Figure 10A:
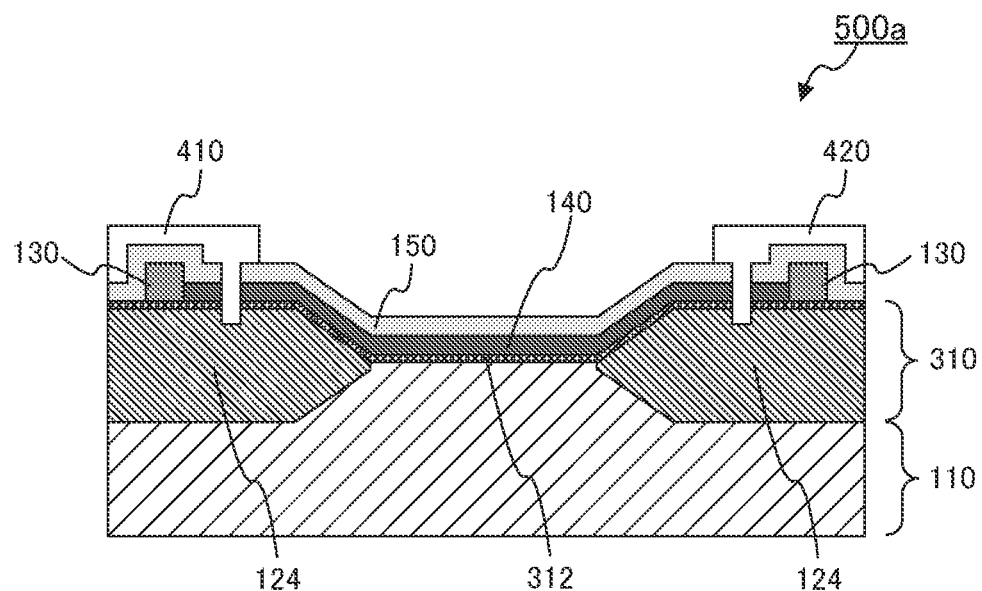
FIGS. 10A and 10B are sectional views illustrating configurations of a CNT-FET according to Embodiment 4.
Figure 10B:
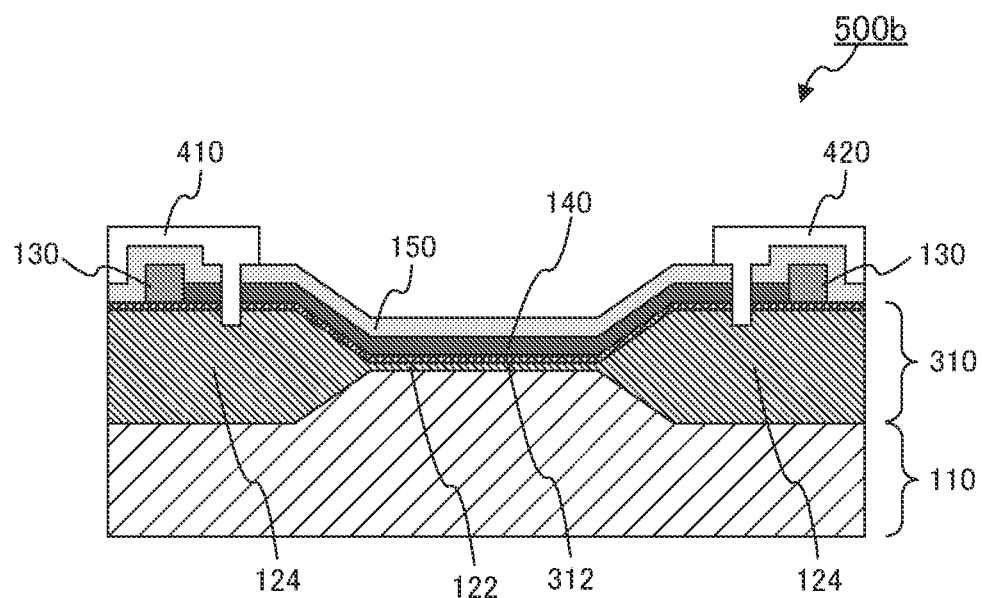

FIGS. 10A and 10B are sectional views illustrating configurations of a CNT-FET according to Embodiment 4. In FIGS. 10A and 10B, CNT-FET 500 includes silicon substrate 110, insulating film 310, catalyst layer 130, CNT 140, protective film 150, source electrode 410, drain electrode 420, and gate electrode 180 (not illustrated).

Insulating film 310 includes a thin insulating film in the channel and a thick insulating film in the contact regions. The insulating film in the channel region is formed of a thin high-permittivity insulating film 312 (see FIG. 10A), or formed of a thin high-permittivity insulating film 312 and of a thin silicon oxide film 122 (see FIG. 10B). The insulating film in the contact regions is formed of a thick silicon oxide film 124 and of a thin high-permittivity insulating film 312.

Source electrode 410 and drain electrode 420 are arranged on protective film 150 in the respective contact regions. Source electrode 410 and drain electrode 420 contact an end surface of CNT 140 via respective contact holes formed in protective film 150 (end-contact structure).

With reference to the illustrations of FIGS. 11A to 11G, a method of manufacturing CNT-FET 500 according to this embodiment will be described below. Steps other than the step of forming high-permittivity insulating film 312, step of forming contact holes, and step of forming source electrode 410 and drain electrode 420 are identical to the respective steps in the method of manufacturing CNT-FET 100 according to Embodiment 1.

Figure 11D:
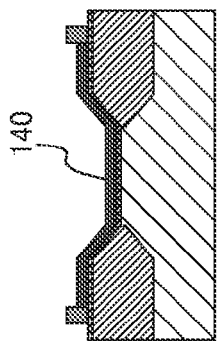
FIGS. 11A to 11G are schematic views illustrating a method of manufacturing a CNT-FET according to Embodiment 4.
Figure 11C:
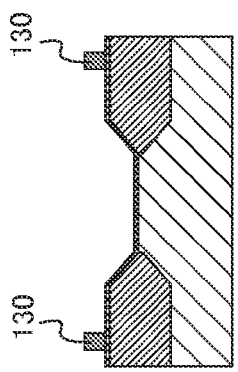
Figure 11G:
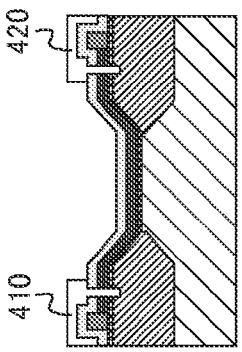
Figure 11B:
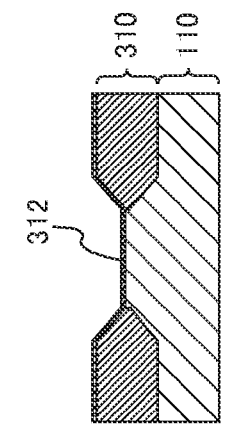
Figure 11F:
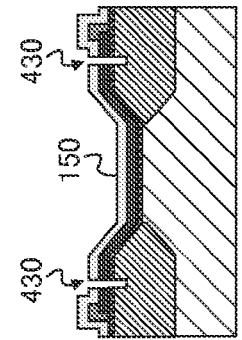
Figure 11A:
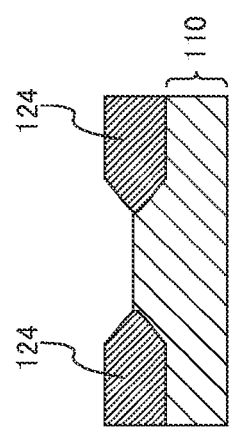

First, thick silicon oxide film 124 is formed on silicon substrate 110 in the contact regions (see FIG. 11A). Next, high-permittivity insulating film 312 is formed on the silicon substrate 110 (see FIG. 11B). Next, catalyst layer 130 for growing CNT 140 is formed on high-permittivity insulating film 312 in the contact regions (see FIG. 11C). CNT 140 is then grown from catalyst layers 130 (see FIG. 11D). Protective film 150 is formed in such a way as to cover CNT 140 (see FIG. 11E). Next, contact holes 430 that extend substantially perpendicularly to the substrate surface are formed in protective film 150 in the respective contact regions, exposing end surfaces of CNT 140 (see FIG. 11F). Next, source electrode 410 and drain electrode 420 are formed on protective film 150 in the respective contact regions so that they are electrically connected to the end surfaces of CNT 140 via respective contact holes 430. Finally, gate electrode 180 is formed at a desired position.

Furthermore, in the procedure described above, by forming a thin silicon oxide film in the channel region before the step of forming high-permittivity insulating film 312 (see FIG. 11B), it is possible to manufacture CNT-FET 500b according to this embodiment (a CNT-FET in which the insulating film in the channel region is formed of a thin high-permittivity insulating film and of a thin silicon oxide film; see FIG. 10B).

Furthermore, in the procedure described above, by performing wet etching before the step of forming source electrode 410 and drain electrode 420 (see FIG. 11G), it is possible to manufacture a CNT-FET 400 in which a source electrode and a drain electrode contact an end surface and a side surface in the vicinity of the end surface of the CNT.

Thus, since the insulating film in the channel region in the CNT-FET according to this embodiment includes a high-permittivity insulating film, it is possible to make the insulating film in the channel region thinner while providing the effects of the CNT-FET according to Embodiment 3. Thus, the CNT-FET according to this embodiment exhibits excellent trans-conductance.

(Embodiment 5)

Embodiment 5 is directed to a biosensor having a CNT-FET (back-gate type) according to Embodiment 4. The same components as those of the CNT-FETs according to Embodiments 1 to 4 are given the same reference signs and duplicate description is omitted.

Figure 12:
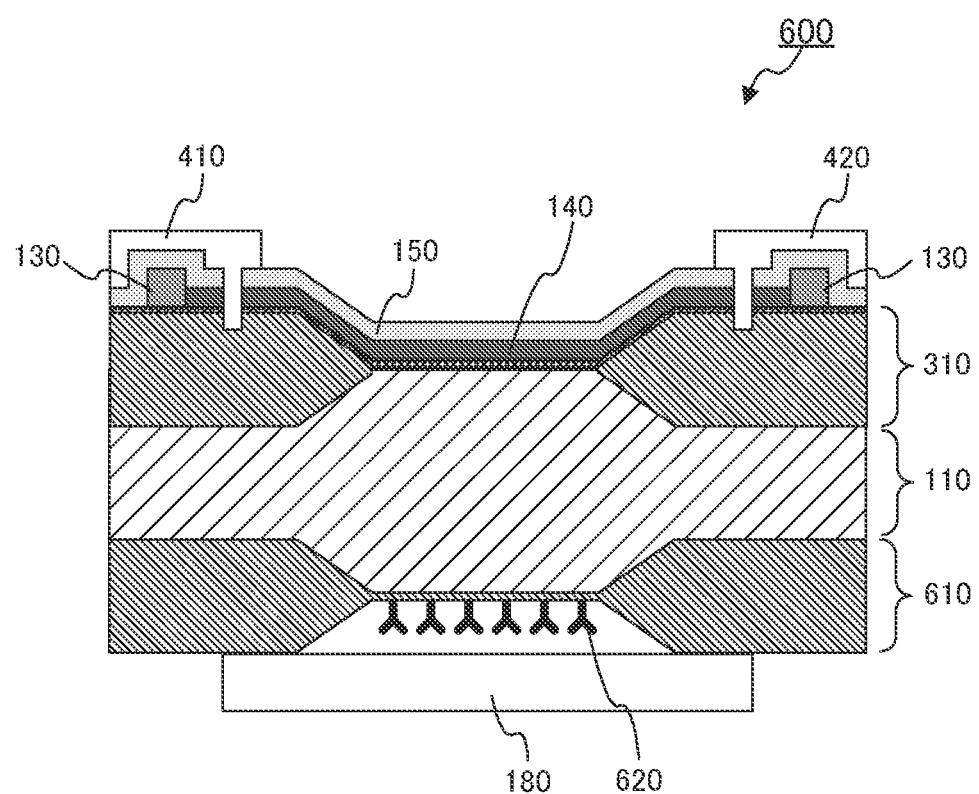
FIG. 12 is a sectional view illustrating a configuration of a biosensor according to Embodiment 5.

FIG. 12 is a sectional view illustrating a configuration of a biosensor according to Embodiment 5. In FIG. 12, biosensor 600 includes silicon substrate 110, insulating film 310, second insulating film 610, catalyst layer 130, CNT 140, protective film 150, source electrode 410, drain electrode 420, gate electrode 180, and target recognition molecule 620. Components other than second insulating film 610 and target recognition molecule 620 are identical to the respective components of the CNT-FET according to Embodiment 4.

Second insulating film 610 covers the rear side of silicon substrate 110 (surface not including CNT 140). Second insulating film 610 in the reaction region is formed of a thin silicon oxide film, and second insulating film 610 surrounding the reaction region is formed of a thick silicon oxide film. As a result, the reaction region is shaped in a concave shape.

Target recognition molecule 620 is a molecule that specifically binds to a target substance. Target recognition molecule 620 is, for example, an antibody. Target recognition molecule 620 is immobilized to second insulating film 610 in the reaction field.

Gate electrode 180 is arranged in such a way as to cover the reaction field formed on the rear side of silicon substrate 110.

Detection of a target substance by means of biosensor 600 according to this embodiment may be accomplished by feeding a sample solution to the reaction region in which target recognition molecule 620 is immobilized, arranging gate electrode 180 so as to cover the reaction region, applying voltage to gate electrode 180, and measuring changes in electrical characteristics (e.g., $I_{ds}$-$V_g$ characteristics) between source electrode 410 and drain electrode 420.

Thus, since the CNT is protected and also the insulating film (high-permittivity insulating film) in the channel region is made thin in the biosensor according to this embodiment, the biosensor is capable of stable, high-precision detection.

(Embodiment 6)

Embodiment 6 is directed to a biosensor having a CNT-FET (side-gate type) according to Embodiment 4. The same components as those of the biosensor according to Embodiment 5 are given the same reference signs and duplicate description is omitted.

Figure 13:
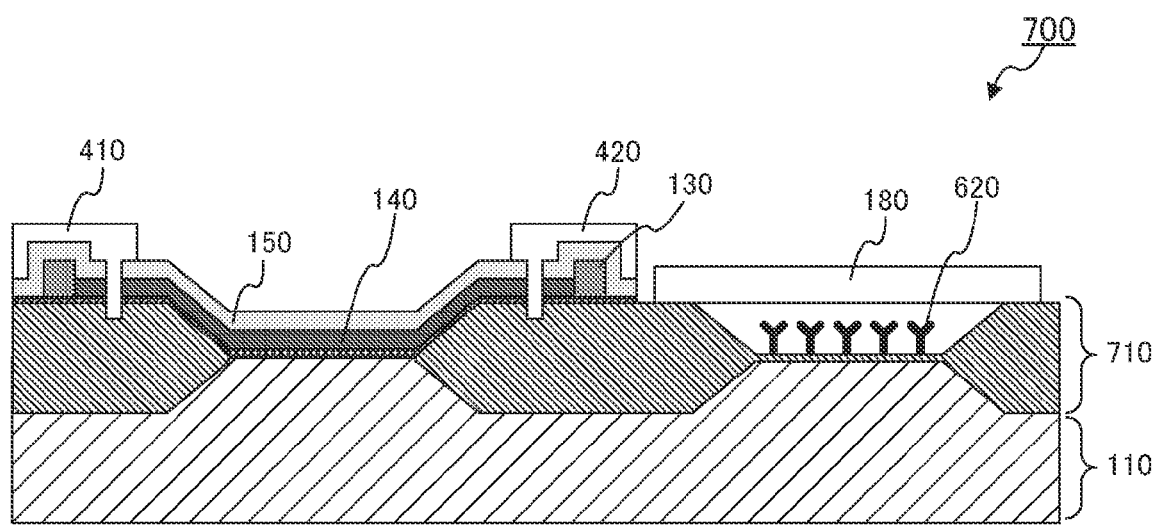
FIG. 13 is a sectional view illustrating a configuration of a biosensor according to Embodiment 6.

FIG. 13 is a sectional view illustrating a configuration of a biosensor according to Embodiment 6. In FIG. 13, biosensor 700 includes silicon substrate 110, insulating film 710, catalyst layer 130, CNT 140, protective film 150, source electrode 410, drain electrode 420, gate electrode 180, and target recognition molecule 620. The biosensor according to Embodiment 6 differs from the biosensor according to Embodiment 5 in terms of the position of gate electrode 180 and target recognition molecule 620.

Insulating film 710 covers the front side of silicon substrate 110 (surface including CNT 140). Insulating film 710 in the channel region is formed of a thin high-permittivity insulating film, and insulating film 710 in the contact regions is formed of a thick silicon oxide film and of a thin high-permittivity insulating film. Insulating film 710 in the reaction region is formed of a thin silicon oxide film, and insulating film 710 surrounding the reaction region is formed of a thick silicon oxide film. As a result, the reaction region is shaped in a concave shape.

Target recognition molecule 620 is immobilized to second insulating film 710 in the reaction field.

Gate electrode 180 is arranged in such a way as to cover the reaction field formed on the front side of silicon substrate 110.

Detection of a target substance by means of biosensor 700 according to this embodiment may be accomplished by feeding a sample solution to the reaction region in which target recognition molecule 620 is immobilized, arranging gate electrode 180 so as to cover the reaction region, applying voltage to gate electrode 180, and measuring changes in electrical characteristics (e.g., $I_{ds}$-$V_g$ characteristics) between source electrode 410 and drain electrode 420.

Similarly to the biosensor according to Embodiment 5, the biosensor according to this embodiment is capable of stable, high-precision detection.

(Embodiment 7)

Embodiment 7 is directed to a biosensor having a CNT-FET (top-gate type) according to Embodiment 2. The same components as those of the biosensors according to Embodiments 5 and 6 are given the same reference signs and duplicate description is omitted.

Figure 14:
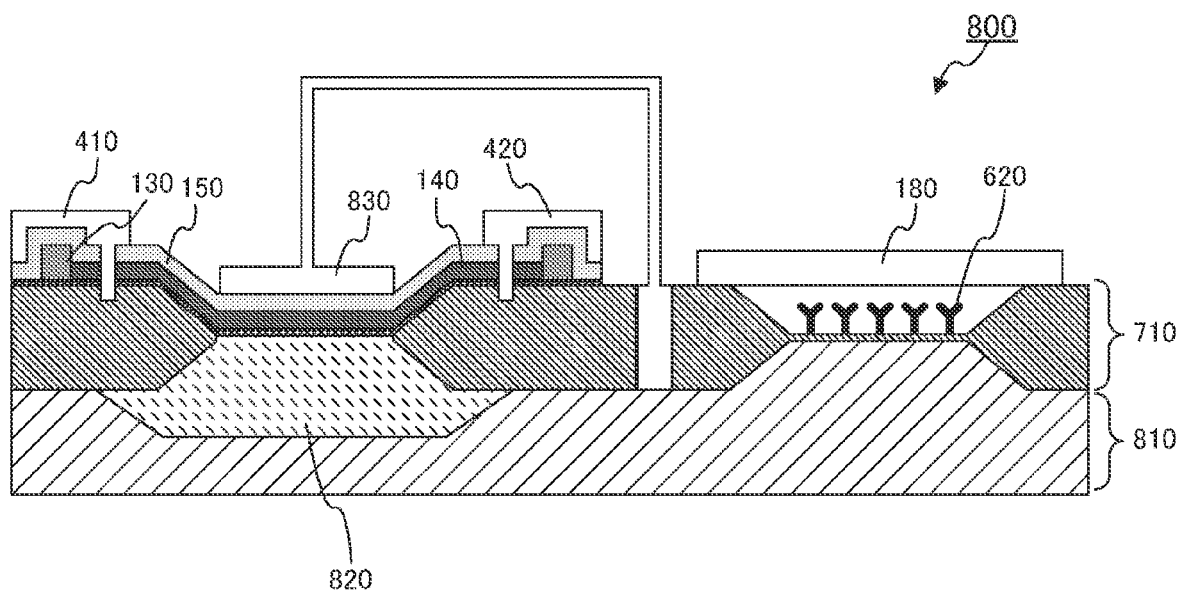
FIG. 14 is a sectional view illustrating a configuration of a biosensor according to Embodiment 7.

FIG. 14 is a sectional view illustrating a configuration of a biosensor according to Embodiment 7. In FIG. 14, biosensor 800 includes p-type silicon substrate 810, insulating film 710, catalyst layer 130, CNT 140, protective film 150, source electrode 410, drain electrode 420, gate electrode 180, target recognition molecule 620, and top gate member 830.

Silicon substrate 810 is a substrate made of p-type silicon, and has an insulating film on its surface. Moreover, p-type silicon substrate 810 has n-type diffusion layer 820 in the channel region. A method of manufacturing a semiconductor substrate having an n-type diffusion layer may be appropriately chosen from methods known in the art, such as ion implantation.

Top gate member 830 is arranged on protective film 150 in the channel region, and is connected to p-type silicon substrate 810.

Detection of a target substance by means of biosensor 800 according to this embodiment may be accomplished by feeding a sample solution to the reaction region in which target recognition molecule 620 is immobilized, arranging gate electrode 180 so as to cover the reaction region, applying voltage to gate electrode 180, and measuring changes in electrical characteristics (e.g., $I_{ds}$-$V_g$ characteristics) between source electrode 410 and drain electrode 420.

Similarly to the biosensors according to Embodiments 5 and 6, the biosensor according to this embodiment is capable of stable, high-precision detection.

Hereinafter, Examples of the present invention will be described, which however shall not be construed as limiting the scope of the invention thereto.

EXAMPLES

1. Manufacture of CNT-FET

First, by the LOCOS process, a 500 nm-thick silicon oxide film is formed on a silicon substrate (size: 20 mm×20 mm, thickness: 0.55 mm) in the contact regions (see FIG. 11A). The silicon oxide film deposited in the channel region is etched away using an etchant containing hydrofluric acid. A 50 nm-thick hafnium oxide film (high-permittivity insulating film) is then deposited on the silicon substrate by ALD. Deposition temperature is set at 175° C.

After formation of the hafnium oxide film, a resist pattern is formed on the hafnium oxide film by photolithography, covering areas of the substrate surface other than catalyst formation areas with a resist film (OFPR800, TOKYO OHKA KOGYO CO., LTD.). A layer of silicon is deposited on the resist film-deposited areas of the substrate to a thickness of 20 nm, a layer of aluminum is deposited on the silicon layer to a thickness of 5 nm, a layer of iron is deposited on the aluminum layer to a thickness of 2 nm, and a layer of molybdenum is deposited on the iron layer to a thickness of 0.3 nm. By a liftoff process, catalysts (size: 3 μm×10 μm each) are formed on the substrate (see FIG. 11C). The catalyst-to-catalyst interval is set at 10 μm. The substrate provided with the catalysts is heated to 900° C. in a mixture gas of methane and hydrogen (thermal CVD), allowing CNTs to grow from the catalysts (see FIG. 11D).

Figure 11E:
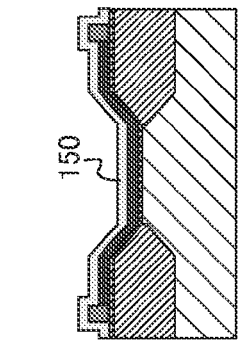

After growing the CNT, a 20 nm-thick hafnium oxide film (protective film) is formed on the silicon substrate and on the CNT by ALD (see FIG. 11E). Deposition temperature is set at 175° C.

After formation of the protective film, a resist pattern is formed on the silicon substrate by photolithography, covering areas of the substrate surface other than a source electrode formation area and a drain electrode formation area with a resist film. Subsequently, by dry etching, areas of the protective film corresponding to the source electrode formation area and to the drain electrode formation area are removed while severing the CNT (see FIG. 11F). At this point, a part of the hafnium oxide film (high-permittivity insulating film) beneath the CNT is over-etched. After dry etching, a layer of titanium is deposited on the substrate to a thickness of 30 nm, and a layer of gold is deposited on the titanium layer to a thickness of 60 nm. By a liftoff process, a source electrode and a drain electrode are formed on the substrate (see FIG. 11G).

Figure 15A:
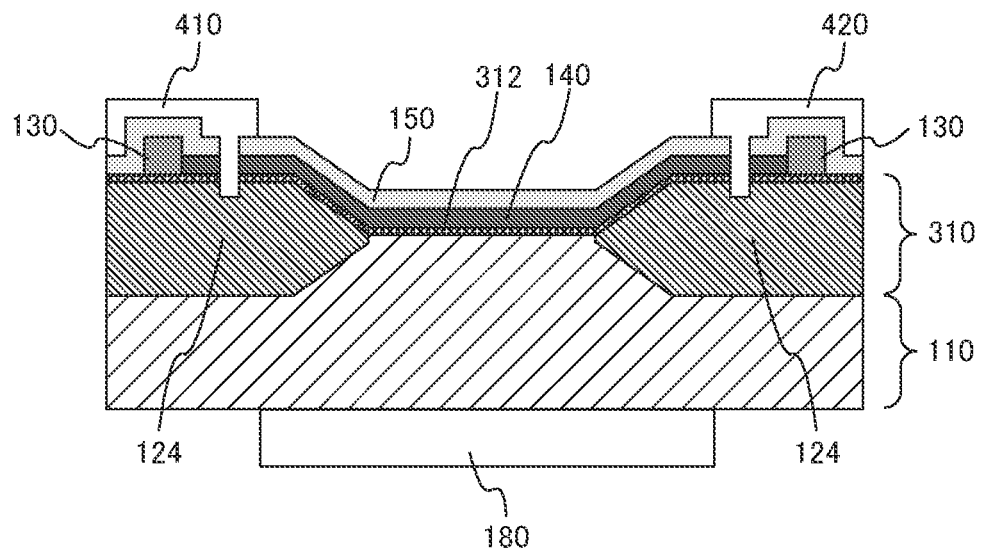
FIGS. 15A and 15B are sectional views illustrating configurations of a CNT-FET manufactured in Example.

After removing the silicon oxide film on the rear side of the silicon substrate by wet etching, a 100 nm-thick aluminum film is deposited to form a gate electrode. FIG. 15A is a sectional view illustrating a configuration of a CNT-FET of the present invention thus manufactured.

2. Manufacture of CNT-FET of Comparative Example

First, a 300 nm-thick silicon oxide film is formed on one side of a silicon substrate (size: 20 mm×20 mm, thickness: 0.55 mm).

Figure 15B:
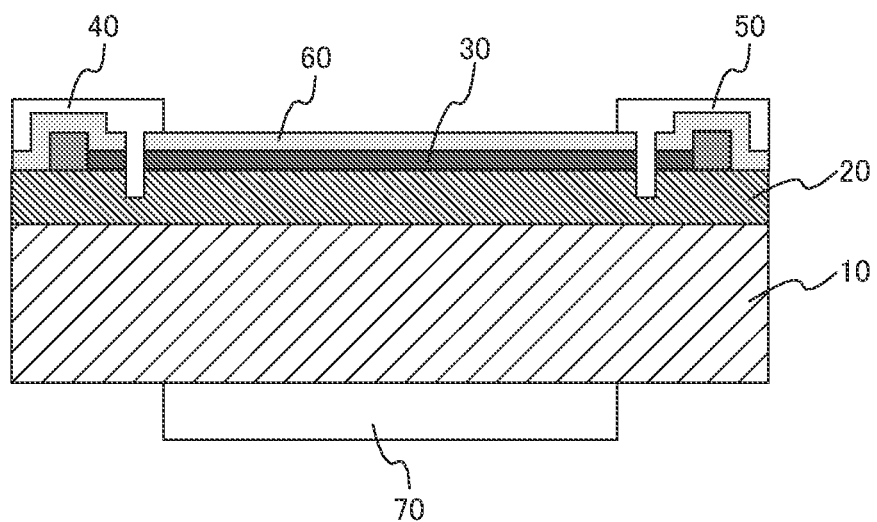

Similarly to the manufacturing method of the present invention, catalysts are formed on the silicon oxide film and CNTs are grown from the catalysts. Similarly to the manufacturing method of the present invention, after formation of a 20 nm-thick hafnium oxide film (protective film), a resist pattern is formed on the silicon substrate by photolithography, and then areas of the protective film corresponding to the source electrode formation area and to the drain electrode formation area are removed while severing the CNT by dry etching. A source electrode and a drain electrode are formed on the protective film by a deposition process and a liftoff process. Finally, a gate electrode is formed on the rear side of the silicon substrate. FIG. 15B is a sectional view illustrating a configuration of a CNT-FET of Comparative Example thus manufactured.

3. Results of Comparison of Electrical Characteristics

Figure 16:
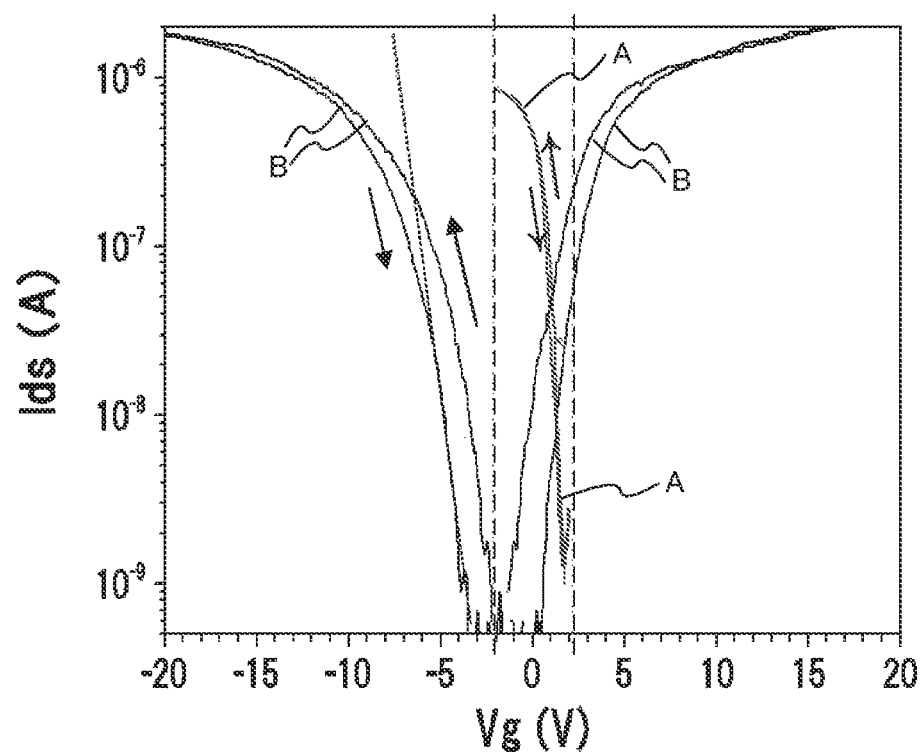
FIG. 16 is a graph of $I_{ds}$-$V_g$ characteristics of CNT-FETs according to the present invention and Comparative Examples.

FIG. 16 is a graph showing electrical characteristics of the CNT-FET of the present invention and electrical characteristics of the CNT-FET of Comparative Example. In the graph, "A" denotes a curve of electrical characteristics of the CNT-FET of the present invention, and "B" denotes electrical characteristics of the CNT-FET of Comparative Example. This graph shows a relationship between gate voltage change and current that flows between the source electrode and drain electrode (source-drain current), when 1V voltage is applied between the source electrode and drain electrode ($I_{ds}$-$V_g$).

When comparing the two CNT-FETs in terms of gate voltage sweep width, it can be seen that the sweep width range needs to be widened to the range from −20V to +20V or so in order for the CNT-FET of Comparative Example to fully function. This is because the insulating film in the channel region is formed of a silicon oxide film and is thick (300 nm). On the other hand, it can be seen that the CNT-FET of the present invention fully functions even when the gate voltage sweep width ranges from −2V to +2V (curve A). This is because the 50 nm-thick hafnium oxide film (specific permittivity: 21) corresponds to a 9 nm-thick silicon oxide film (specific permittivity: 3.9) and is much thinner than the 300 nm-thick silicon oxide film of Comparative Example.

When comparing the two CNT-FETs in terms of hysteretic width, it can be seen that the hysteretic width ΔVh of the CNT-FET of Comparative Example is about 2 V. On the other hand, it can be seen that the hysteretic width ΔVh of the CNT-FET of the present invention is about 0.2, a value much smaller than the hysteretic width ΔVh of the CNT-FET of Comparative Example. For its small hysteretic width, the CNT-FET of the present invention is considered to operate stably.

When comparing the two CNT-FETs in terms of S value ($S=(d \log_{10} I_{ds}/d V_g)^{-1}$), which indicates sub-threshold, the S value of the CNT-FET of Comparative Example is 1,200 mV/dec. On the other hand, the S value of the CNT-FET of the present invention is 500 mV/dec. S value is a measure of current transfer ratio, and smaller values are preferable.

When comparing the two CNT-FETs in terms of trans-conductance (gm) as measured when 1 V voltage is applied between the source electrode and drain electrode, gm of the CNT-FET of Comparative Example is about 0.2 μS. On the other hand, the trans-conductance of the CNT-FET of the present invention is about 0.6 μS. In view of the fact that the two CNT-FETs have the same CNT diameter, it can be seen that CNT-FET the present invention exhibits superior trans-conductance compared to the CNT-FET of Comparative Example even when their trans-conductance is standardized by the CNT diameter.

This application is entitled and claims the priority of Japanese Patent Application No. 2009-003628 filed on Jan. 9, 2009, the disclosure of which including the specification and drawing is herein incorporated by reference in its entirety.

INDUSTRIAL APPLICABILITY

The present invention can manufacture a CNT-FET that stably exhibits excellent electrical conduction properties with good reproducibility, and therefore is useful for the manufacture of integrated circuits and biosensors that have CNT-FETs.

REFERENCE SIGNS LIST

10 Silicon Substrate
20 Gate Oxide Film
30 CNT
40 Source Electrode
50 Drain Electrode
60 Protective Film
70 Gate Electrode
100, 300, 400, 500 CNT-FET
110, 810 Silicon Substrate
120, 310, 710 Insulating film 122 Silicon Oxide Film in Channel Region
124 Silicon Oxide Film in Contact Region
130 Catalyst Layer
140 CNT
150 Protective Film
160, 410 Source electrode
170, 420 Drain electrode
180 Gate Electrode
210 Silicon Oxide Film
220 Silicon Nitride Film
312 High-Permittivity Insulating film
430 Contact Hole
600, 700, 800 Biosensor
610 Second Insulating film
620 Target Recognition Molecule
820 N-type Diffusion Layer
830 Top Gate Member

The invention claimed is:

1. A field effect transistor comprising:
a silicon substrate;
an insulating film covering one side of the silicon substrate;
a source electrode and a drain electrode arranged on or over the insulating film;
a channel formed of a carbon nanotube, the channel connecting the source electrode and the drain electrode; and
a protective film covering the carbon nanotube,
wherein a thickness of the insulating film in a region including the carbon nanotube is smaller than a thickness of the insulating film in regions respectively including the source electrode and the drain electrode,
the source electrode and the drain electrode are arranged on the protective film,
the source electrode is connected to a first end surface of the carbon nanotube via a contact hole formed in the protective film, and
the drain electrode is connected to a second end surface of the carbon nanotube via a contact hole formed in the protective film.

2. A field effect transistor comprising:
a silicon substrate;
an insulating film covering one side of the silicon substrate;
a source electrode and a drain electrode arranged on or over the insulating film;
a channel formed of a carbon nanotube, the channel connecting the source electrode and the drain electrode; and
a protective film covering the carbon nanotube,
wherein a thickness of the insulating film in a region including the carbon nanotube is smaller than a thickness of the insulating film in regions respectively including the source electrode and the drain electrode,
the source electrode and the drain electrode are arranged on the protective film,
the source electrode is connected to a first end surface of the carbon nanotube and to a side surface of the carbon nanotube in the vicinity of the first end surface via a contact hole formed in the protective film, and
the drain electrode is connected to a second end surface of the carbon nanotube and to a side surface of the carbon nanotube in the vicinity of the second end surface via a contact hole formed in the protective film.

3. A method of manufacturing a field effect transistor having a channel formed of a carbon nanotube, comprising:
providing a silicon substrate;
forming a silicon oxide film on the silicon substrate in a source electrode formation region and a drain electrode formation region by a LOCOS process;
forming an insulating film on the silicon substrate in a carbon nanotube formation region, the insulating film being thinner than the silicon oxide film;
providing a carbon nanotube on the insulating film;
forming a protective film on the carbon nanotube; and
forming a source electrode and a drain electrode on the protective film so that the source electrode and the drain electrode can be electrically connected to the carbon nanotube,
wherein forming the source electrode and the drain electrode comprises:
forming contact holes in the protective film in the source electrode formation region and the drain electrode formation region, respectively, to expose a part of the carbon nanotube;
forming the source electrode on the protective film in the source electrode formation region so that the source electrode can be electrically connected to the carbon nanotube via the contact hole; and
forming the drain electrode on the protective film in the drain electrode formation region so that the drain electrode can be electrically connected to the carbon nanotube via the contact hole.

4. A biosensor comprising:
a field effect transistor; and
a target recognition molecule,
wherein the field effect transistor comprising: a silicon substrate; an insulating film covering one side of the silicon substrate; a source electrode and a drain electrode arranged on or over the insulating film; a channel formed of a carbon nanotube, the channel connecting the source electrode and the drain electrode; and a protective film covering the carbon nanotube, wherein a thickness of the insulating film in a region including the carbon nanotube is smaller than a thickness of the insulating film in regions respectively including the source electrode and the drain electrode,
the target recognition molecule is immobilized either on the insulating film that covers one side of the silicon substrate or on a second insulating film that covers the other side of the silicon substrate, and
a thickness of the insulating film or the second insulating film in a region in which the target recognition molecule is immobilized is smaller than a thickness of the insulating film or the second insulating film surrounding the region in which the target recognition molecule is immobilized.

* * * * *